US005976612A

United States Patent [19]
Tardoni

[11] Patent Number: 5,976,612
[45] Date of Patent: Nov. 2, 1999

[54] APPARATUS AND METHOD FOR OPTIMIZING A COMPRESSED AIR SYSTEM

[75] Inventor: James E. Tardoni, Johnstown, Pa.

[73] Assignee: Concurrent Technologies Corporation, Johnstown, Pa.

[21] Appl. No.: 08/997,216

[22] Filed: Dec. 23, 1997

Related U.S. Application Data

[60] Provisional application No. 60/034,184, Dec. 26, 1996.

[51] Int. Cl.[6] ................................. B05D 1/02; B05B 7/00
[52] U.S. Cl. ........................ 427/8; 427/10; 427/421; 239/61; 239/63; 239/73; 239/341; 239/351
[58] Field of Search ...................... 427/8, 10, 421; 239/8, 61, 63, 67, 73, 341, 351; 73/195

[56] References Cited

U.S. PATENT DOCUMENTS

| | | | |
|---|---|---|---|
| 3,949,053 | 4/1976 | Gentry et al. | 423/210 |
| 4,278,205 | 7/1981 | Binoche . | |
| 4,569,480 | 2/1986 | Levey . | |
| 4,915,599 | 4/1990 | Katsuyama et al. . | |
| 4,986,659 | 1/1991 | Bachalo . | |
| 4,988,286 | 1/1991 | Hersh | 431/175 |
| 5,004,159 | 4/1991 | Kistner . | |
| 5,054,687 | 10/1991 | Burns et al. . | |
| 5,058,805 | 10/1991 | Anderson et al. . | |
| 5,074,237 | 12/1991 | Ogasawara . | |
| 5,100,060 | 3/1992 | Haferkorn . | |
| 5,119,992 | 6/1992 | Grime . | |
| 5,134,961 | 8/1992 | Giles et al. | 118/684 |
| 5,135,172 | 8/1992 | Toth . | |
| 5,218,211 | 6/1993 | Cresswell et al. . | |
| 5,240,181 | 8/1993 | Uribe . | |
| 5,284,299 | 2/1994 | Medlock . | |
| 5,333,506 | 8/1994 | Smith et al. . | |
| 5,452,855 | 9/1995 | Keller . | |
| 5,471,298 | 11/1995 | Moriya . | |
| 5,478,014 | 12/1995 | Hynds . | |
| 5,499,198 | 3/1996 | Gaidos et al. | 364/555 |
| 5,546,183 | 8/1996 | Fegley et al. . | |
| 5,561,515 | 10/1996 | Hairston et al. . | |
| 5,601,235 | 2/1997 | Booker et al. | 239/4 |
| 5,619,324 | 4/1997 | Harvill et al. . | |

*Primary Examiner*—Shrive Beck
*Assistant Examiner*—Michael Barr
*Attorney, Agent, or Firm*—Draughon PA; Mark J. Young; C. Joan Gilsdorf

[57] ABSTRACT

The invention relates to a method and apparatus for optimizing the transfer efficiency of a compressed air system used to apply liquid coatings (e.g., paint) while producing a high quality film coating. The invention uses a laser measuring system to determine the atomization of a spray produced by a compressed air spray system. The system also monitors and measures the liquid and air being supplied to the spray applicator to determine the settings required for optimization.

29 Claims, 4 Drawing Sheets

APPARATUS AND METHOD FOR OPTIMIZING A COMPRESSED AIR SYSTEM

This Application claims the benefit of U.S. Provisional Application No. 60/034,184, filed Dec. 26, 1996.

BACKGROUND

The present invention relates to an apparatus and method for optimizing a compressed air system used to apply liquid coatings while producing a high quality film coating.

Industries that apply liquid coatings cover a wide range of products including automotive, containers, furniture, machinery, aircraft, electronics, and shipbuilding. Approximately 1 billion gallons of liquid coatings are applied annually in the United States. About 10 percent of these liquid coatings are applied using conventional low-volume, high pressure, compressed air systems (CAS).

Compressed air spray systems have been in use for over 40 years. CAS systems use high pressure (40–70 pounds per square inch [psi]) air to atomize a liquefied stream of paint. The high energy air stream is mixed with paint, producing an atomization that is generally very fine and easily applied. Thus, the system is capable of producing a very good finish with high quality visual characteristics while easily covering a large surface area in a relatively short time span.

A disadvantage associated with CAS systems is that the high degree of atomization produces a very fine spray that is highly susceptible to overspray. Such spray characteristics result in more paint being used to compensate for overspray waste and a relatively inefficient transfer efficiency (TE) of approximately 20 to 40 percent (TE=percentage of coating gained on a sprayed part relative to the weight of coating sprayed).

Another disadvantage associated with CAS systems concerns volatile organic compounds (VOC) emissions. The consistency of most coatings is too thick for effective spray application. Thinners or solvents are introduced to decrease viscosity and thereby facilitate spray application. Examples of such thinners and solvents include petroleum spirits, mineral spirits, toluene, xylene, solvent naphtha, esters, alcohols and ketones. The high degree of atomization and relatively low transfer efficiency associated with CAS systems is conducive to relatively high levels of VOC emissions from the solvents and thinners.

Concern over VOC emissions and paint overspray has led to the development of High Volume Low Pressure (HVLP) spraying systems. An HVLP system delivers paint using a large volume of air (100 cfm) while operating at a relatively low air pressure, typically between 3 to 6 psi and not exceeding 10 psi. A CAS system typically operates between 45 to 60 psi. The low pressure high volume design of the HVLP system produces a transfer efficiency as high as 85% due mainly to the larger droplet size distributions of the spray. Large droplets and high transfer efficiency translate into reduced VOC emissions and paint consumption.

Environmental concerns over VOC emissions have led some local governments to require the use of HVLP spray systems. Southern California and the San Francisco Bay area each promulgated rules requiring the use of HVLP spray systems while applying refinish materials.

HVLP systems have several disadvantages. HVLP paint spray systems use large volumes of air and energy in comparison to CAS systems. HVLP systems also require most coatings to be greatly thinned to produce an acceptable spray. If excessive thinning is required, an operator may need to apply multiple coats to produce a desired finish. High viscosity paints such as latex may be too thick for an HVLP system. HVLP systems are also inappropriate for spraying large areas since the rate of application is relatively low in comparison to compressed air systems. Furthermore, the coating quality generated from HVLP systems, when operated at recommended settings is unsatisfactory to many users. As a result, many commercial spray coating facilities compensate by increasing the air flow rate above the recommended settings in an attempt to improve atomization and coating quality. Elevated air flow rates increase overspray, waste, and energy usage when the HVLP system is modified.

Thus, there is a continuing need for an optimized compressed air system which can achieve the high transfer efficiencies of an HVLP spray system while producing a high quality coating.

SUMMARY

An object of the present invention is to provide an apparatus and method for optimizing an atomized spray of a compressed air liquid spray system. Once optimized, a CAS system is capable of producing a desired transfer efficiency with a high quality film coating. Optimization is said to occur when the spray device achieves a desired transfer efficiency. The desired transfer efficiency is generally the maximum efficiency which corresponds to acceptable coating qualities and spray characteristics for a given system. Another object of the present invention is to enable a CAS system to produce a transfer efficiency substantially equal to an HVLP system while delivering a superior coating quality and application rate, as well as energy savings and reduced VOC emissions.

Atomization and transfer efficiency are interrelated. For any given atomization there is a corresponding transfer efficiency. This relationship is independent of any spray system or spray gun configuration, at a given spray distance and spray work piece geometry. A cross correlation between transfer efficiency and atomization can be made utilizing gas pressure as a reference. For example, gas pressure X corresponds to transfer efficiency Y and atomization Z. The plotted graph reveals a curve which is independent of the spray system used. The cross correlated data reveals that as the average size of the droplets within the atomized spray increases, the transfer efficiency also increases. Using this relationship, the present invention is capable of measuring and determining the optimized atomization for a CAS spray system.

The optimizing apparatus determines the atomization of any given spray using a computer aided laser particle sizing apparatus measuring system. The method of determining an optimized atomization includes the steps of measuring atomization created by the spray applicator at various pressures, experimentally measuring transfer efficiencies at similar pressures, cross correlating atomization and transfer efficiency using pressure as a reference and adjusting the apparatus to achieve the calculated atomization which relates to the desired transfer efficiency.

The optimizing apparatus further includes a liquid system side and a gas system side. Fluid flow parameters are monitored and controlled on both sides. The liquid system side of the apparatus includes a liquid pot, a metering pump with speed control and a mass flow meter. The gas system side of the apparatus includes a gas source, a pressure regulator, a manifold with pressure and temperature instrumentation, a flow rate measurement and control device and pressure instrumentation. Both the liquid and gas systems connect to a spray applicator.

DESCRIPTION

Figure 1:
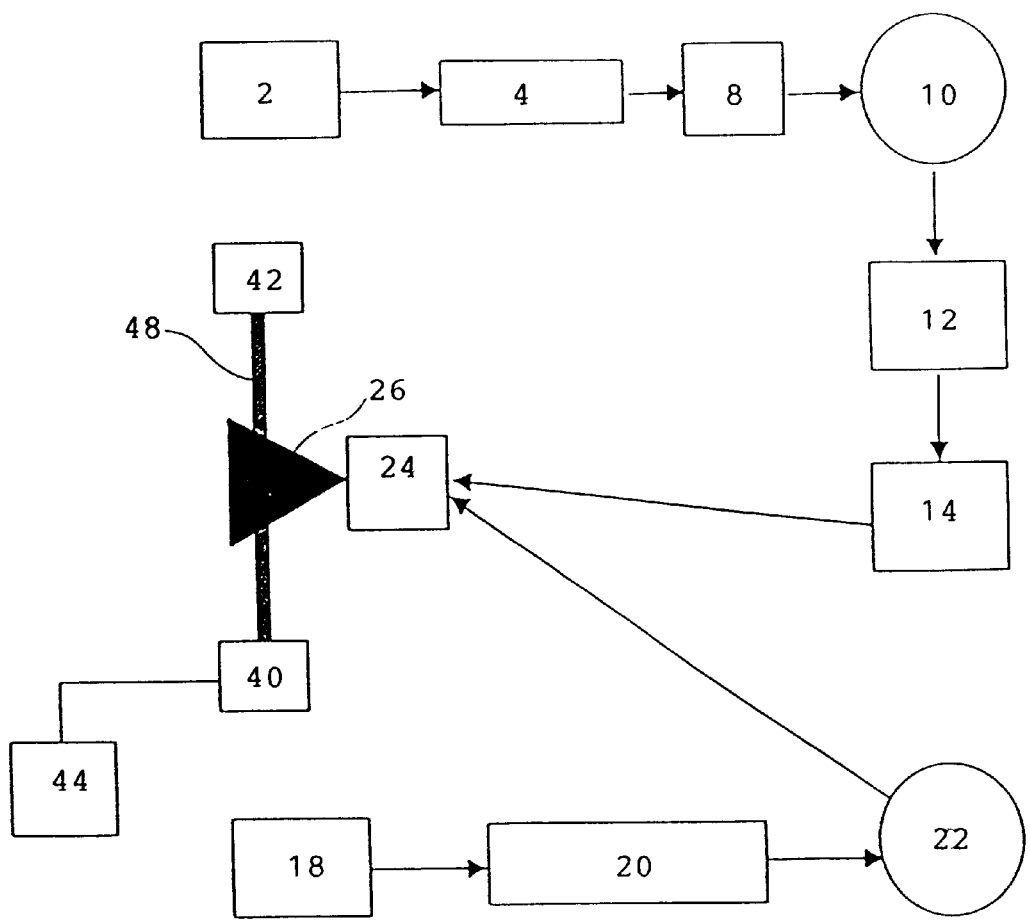
FIG. 1 is an overview of the Optimizing Apparatus.

The Optimized Spray Device (OSD) apparatus is designed and developed to achieve a range of desired liquid transfer efficiency settings. By proper control and measurement of the fluids flowing to the spray applicator, an optimized atomization can be measured and determined for a desired transfer efficiency. Once an optimized atomization is determined, a particular spray device can be set to produce an optimized atomization and its corresponding desired transfer efficiency.

Optimization occurs when the spray device achieves a desired transfer efficiency. For example, if the goal is to achieve an HVLP 90% TE then the optimized atomization would be the measured atomization of spray that produced the desired 90% TE. The optimized atomization for the desired 90% TE can either be determined experimentally or derived from existing experimental data. Since the relationship between atomization and transfer efficiency is independent of the spray system used, the experimental data need not be derived from an HVLP spray system.

The apparatus of the present invention includes a compressed air system, means for measuring and controlling fluid flow parameters, and means for measuring liquid spray droplet sizes. Atomization is recorded by the present invention at various liquid flow rates and gas pressures. Based on the recorded atomization data and corresponding liquid flow rates and gas pressures, the fluid flow parameters of a CAS device can be set to produce the optimized atomization corresponding to the desired TE. Once optimized, the CAS device is capable of delivering a spray which produces a high quality coating with an acceptable application rate and minimal waste.

Thus a conventional low-volume, high pressure, compressed air system (CAS) can be optimized to produce a transfer efficiency equal to an HVLP system. CAS systems can also be optimized to emulate any other system so long as the transfer efficiency is known for that particular system.

An optimized CAS system not only reproduces an HVLP system's transfer efficiency, but the overall liquid transfer performance of the CAS system exceeds that of the HVLP system. Table 1 illustrates the superior coating quality of an optimized CAS system as compared to an HVLP system. The optimized CAS system out-performed the HVLP system by 250% in the Mandrel Bend Test. The Mandrel Bend test measures the length of the coating tear after the test panel has been bent 180 degrees. The optimized CAS system also achieved superior results over the HVLP system in the salt spray corrosion tests.

TABLE 1

Product Analysis Report - Performance Comparison of Cold Rolled Steel Pretreated Panels Coated with the Optimized CAS and HVLP Systems

| Sample ID | Test Parameter | Test Result | Test Method |
| --- | --- | --- | --- |
| HVLP 95-4005-*P- | Gloss at 60° | 96.5 | ASTM B499 |
|  | Reverse Impact | Pass at 46 inch lbs. | ASTM D522 |
| HVLP 95-4006-P | Mandrel Bend - 1/8" | Fail - 5/8$^{th}$ inch from small end of the cone | ASTM D522 |
|  | MEK Rub | No effect after 50 double rubs | ASTM D4852 |
| HVLP 95-4007-P | Salt Spray Corrosion | Heavy unscribed surface corrosion | ASTM B117 |
| HVLP 95-4009-P | Pencil Hardness | >8H beyond capabilities of test | ASTM D3363 |
|  | Intercoat Adhesion | No effect after 50 double rubs | ASTM D3359 |
| OPCAS 95-4000-P | Gloss at 60° | 96.5 | ASTM B499 |
|  | Reverse Impact | Pass at 68 inch lbs. | ASTM D522 |
| OPCAS 95-4001-P | Mandrel Bend - 1/8" | Fail - 1/4 inch from small end of cone | ASTM D522 |
|  | MEK Rub | No effect after 50 double rubs | ASTM D4852 |
| OPCAS 95-4002-P | Salt Spray Corrosion | Traces of unscribed surface corrosion | ASTM B117 |
| OPCAS 95-4002-P | Pencil Hardness | >8H beyond capabilities of test | ASTM D3363 |
|  | Intercoat Adhesion | No effect after 50 double rubs | ASTM D3359 |

An optimized CAS spray device can increase transfer efficiency, coating quality, coating application rate, and energy savings over the performance of an HVLP system.

Liquid transfer is the process whereby a fraction of the atomized liquid is deposited on the workpiece under the influence of aerodynamic forces, and in the case of electrostatic systems, electrostatic forces. The balance of the atomized liquid is swept around the workpiece by the airflow and forms overspray. The liquid transfer is best described in terms of atomization performance and drop transfer efficiency performance. The transfer efficiency, TE, is then given by:

$$TE = \int_{Dmin}^{Dmax} T(D)q(D)dD$$

The drop transfer efficiency function, T(D), represents the fraction of drops of diameter D that deposit on the workpiece. The atomization probability density function, q(D), represents the probability of atomizing a liquid volume into drops within the diameter range.

The transfer efficiency equation shows that atomization and drop transfer influence transfer efficiency. The atomization process primarily defines the droplet size distribution in a compressed air system. In the case of air spray guns, a high speed annular flow of air facilitates atomization of a center liquid jet. The resulting shear between the air and liquid disrupts the liquid flow into shreds and ligaments which rapidly collapse into spherical drops due to surface tension.

Atomization performance can be quantified in terms of a measured drop-size distribution using the atomization probability density function for a volume, q(D). Integration of this function over a finite range of diameters yields the probability of atomizing a liquid volume into drops within that diameter range.

In the case of commercial paint atomizers, the drop-size distribution is quite broad (ranging from less than 1 $\mu$m to greater than 100 $\mu$m). The span or spread of the distribution is influenced most strongly by atomizer type and paint formulation. The distributions produced by rotary and supercritical atomizers are generally narrower than those produced by air-spray or airless atomizers. The narrowness is attributed to the variance in dominant atomization mechanisms for each type. Furthermore, paints exhibiting time dependent behavior tend to produce narrower drop-size distributions.

For a particular type of atomizer (air, airless, rotary or supercritical) and paint formulation, the atomization mechanism is qualitatively consistent and there is little variation in the spread of the distribution. Consequently, it is common practice to characterize performance of a particular type of atomizer in terms of mean values of the distribution. The most common is the Sauter Mean Diameter (SMD) which exhibits the same surface to volume ratio as the atomized spray.

The atomization performance, q(D), of an air spray applicator is influenced by (1) the gun configuration, (2) the flow rates and (3) the liquid formulation. The gun consists of a fluid nozzle and an air cap. Manufacturers generally supply various fluid nozzle and air cap combinations for a particular gun. Atomization performance is strongly influenced by these combinations.

Three flow rates affect atomization. The flow rates are the liquid, atomizing air and shaping air. The atomizing and shaping air may be supplied independently to the gun, which allows for excellent control. Alternatively, a common air supply may be split in the body of the applicator with a simple valve arrangement. The atomizing air flow rate has the strongest effect on the atomization performance. The shaping air flow rate has the strongest effect on the pattern shape. The liquid flow rate has the strongest effect on the rate of liquid deposition. The effects of shaping air and liquid flow rates on atomization are secondary.

Liquid formulation also affects atomization. The effect of liquid formulation on atomization is critical. Even relatively small changes in solvent concentration can affect not only the mean values but also the width of the drop-size distribution.

The drop transfer efficiency, T(D), is influenced by the gun configuration and the geometry of the workpiece. The drop transfer efficiency is controlled by the structure of the air flow between the applicator and workpiece. The basic gun design and fluid nozzle and air cap combination establish the initial structure of the air flow between the applicator and workpiece. Of critical importance is the width of the spray along the minor axis of the spray pattern since most of the spray flows parallel to the minor axis. Air spray guns generally produce an elliptical spray pattern. The major axis runs the length of the ellipse between the extremities. The minor axis, perpendicular to the major axis, defines the narrow width of the spray pattern. The structure of the flow near the workpiece is established by the near nozzle flow structure and the shape of the workpiece. In general T(D) increases as the width of the spray in the minor axis decreases, as the separation distance between the applicator and workpiece decreases, and as the size of the workpiece increases up to a critical value.

Variations in paint and air flow rates have little effect on drop transfer efficiency. The basic structure of the flow is established by the nozzle and workpiece geometry and is largely unaffected by the air and liquid flow rates. Flow rates do affect the absolute velocity and consequently the atomization. However, the basic flow structure is largely unaffected by the flow rates. An increase in air velocity around the workpiece (which tends to decrease T(D)) is offset by an increase in the initial momentum imparted to the drops near the nozzle and directed towards the workpiece (which tends to increase T(D)). The net effect on T(D) of increasing the air flow rate is therefore small.

Similar to air flow rate, liquid formulation has little effect on flow structure and hence on T(D). This is in sharp contrast to the effect of liquid formulation on atomization performance, q(D). Indeed, both air flow rate and liquid formulation do have substantial influence on TE through atomization performance, q(D).

Liquid spray droplet size influences both transfer efficiency and coating quality. Transfer efficiency is a function of droplet size. The efficiency drops off rapidly as droplet size decreases. Indeed, small droplets are conducive to overspray. Concomitantly, liquid spray droplet size affects coating uniformity and film quality. Large droplet size often leads to poor uniformity and film quality. Long wavelength, small amplitude disturbances on the coating surface commonly referred to as "orange peel" are attributed to large droplet size. Conversely, dry defects (e.g., granular-like appearance on the coating surface) are associated with small droplet size. An optimized spray exhibits a high TE while producing a high quality coating.

The term "air" is defined as being synonymous with the term "gas" and is intended to encompass the defined meanings of both terms. Thus, the term "air" would encompass the mixture of atmospheric gases such as nitrogen, oxygen, hydrogen, carbon dioxide and argon and all other gases and mixtures thereof. The term "air" is chosen because the term more fully describes the preferred gas used in aiding the atomization process used in the preferred embodiment.

Referring to FIG. 1, the air supply is introduced to the air system through the actuated pressure regulator 4. An incoming pressure instrument 2 can be fluidly connected between the incoming air supply and the pressure regulator 4. The incoming pressure instrument 2 monitors the initial air pressure before the air enters the actuated pressure regulator 4, but the incoming pressure instrument 2 is not essential to the practice of the present invention. The role of the actuated pressure regulator 4 is to control the pressure of the air flowing into the manifold 8. The manifold 8 is fluidly connected to the actuated pressure regulator 4. The manifold 8 equalizes the air pressure before the air enters the flow rate control and measurement instrument 10. The present invention may also be operated without the manifold 8. The actuated control valve 12 is fluidly connected to the measurement instrument 10 and the pressure measuring instrument 14. The actuated control valve 12 adjusts the gas mass flow rate and air pressure before the air is released to the spray applicator 24. The outgoing pressure measuring instrument 14 monitors the gas differential pressure across the spray applicator 24.

The liquid delivery and control system preferably begins at the liquid pot 18. The liquid pot 18 stores a volume of liquid to be atomized by the spray applicator 24. Other storage devices or liquid supply sources may also be used in place of the liquid pot 18. The liquid is delivered and controlled by the metering pump 20. The metering pump 20 inlet is connected to the liquid pot 18 by a hose or pipe and the outlet is connected to the mass flow meter. The mass flow meter 22 monitors the mass flow rate of liquid to the spray applicator 24. The spray applicator 24 facilitates atomization 26 by introducing the gas to the liquid and is fluidly connected to the mass flow meter 22. Atomization 26 created by the spray applicator 24 is measured and quantified by the laser system.

Figure 4:
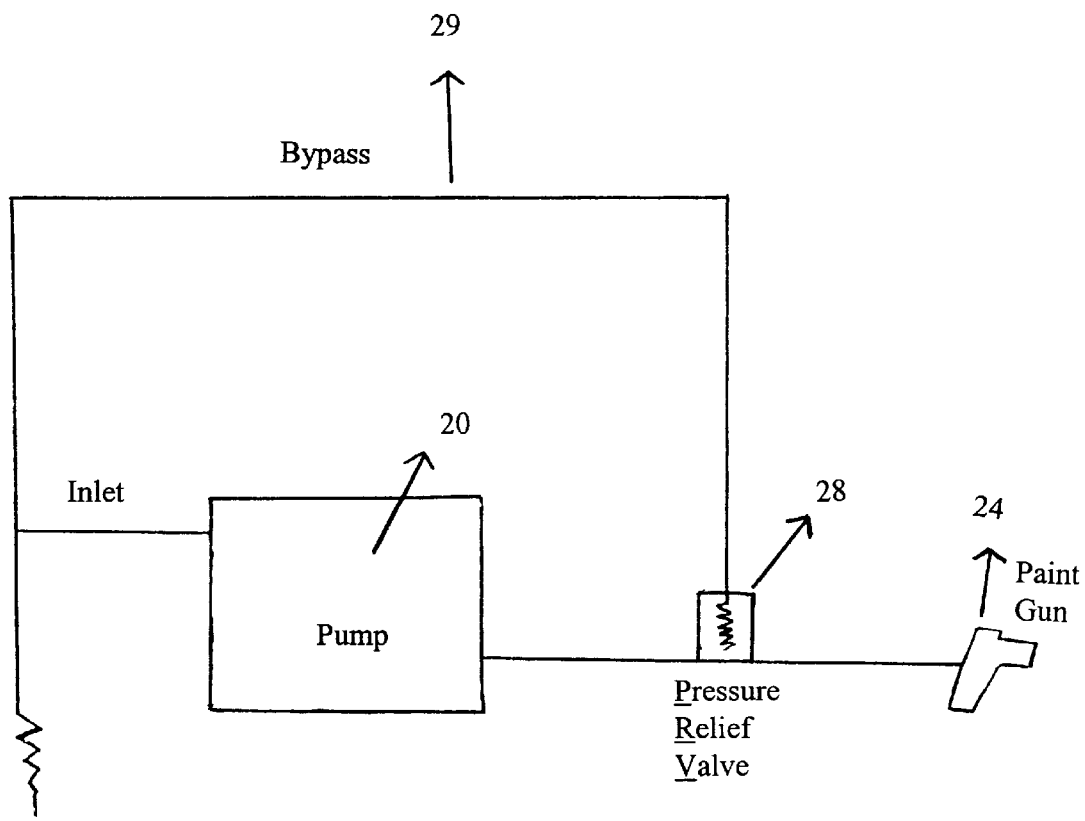
FIG. 4 depicts the fluid bypass system.

An alternative embodiment may include a liquid bypass system as illustrated in FIG. 4. The liquid bypass system enables the metering pump 20 to operate continuously even when the spray applicator 24 is not triggered. The liquid bypass system includes the outlet of the metering pump 20 being fluidly connected to a pressure relief valve 28. The pressure relief valve 28 is fluidly connected to the spray applicator 24 and a bypass line which is connected to the inlet of the metering pump 20. Thus, when the spray applicator 24 is not triggered, pressure builds up in the fluid connection line causing the pressure relief valve 28 to open. Once the pressure relief valve 28 is open, liquid can enter the bypass line 28 and flow back into the metering pump 20. When the spray applicator 24 is triggered, pressure is reduced and the pressure relief valve 28 closes allowing the liquid to flow freely to the spray applicator 24.

The laser particle sizing apparatus measures atomization characteristics using the Fraunhofer diffraction technique. The laser system includes three components: a transmitter 42, a receiver 40, and a computer 44. The transmitter 42 houses the laser. The receiver 40 includes a receiving lens, receiving plate and housing with horizontal and vertical adjustments. The receiver 40 can be fitted with different lenses depending on the range of droplet sizes to be measured.

Figure 2:
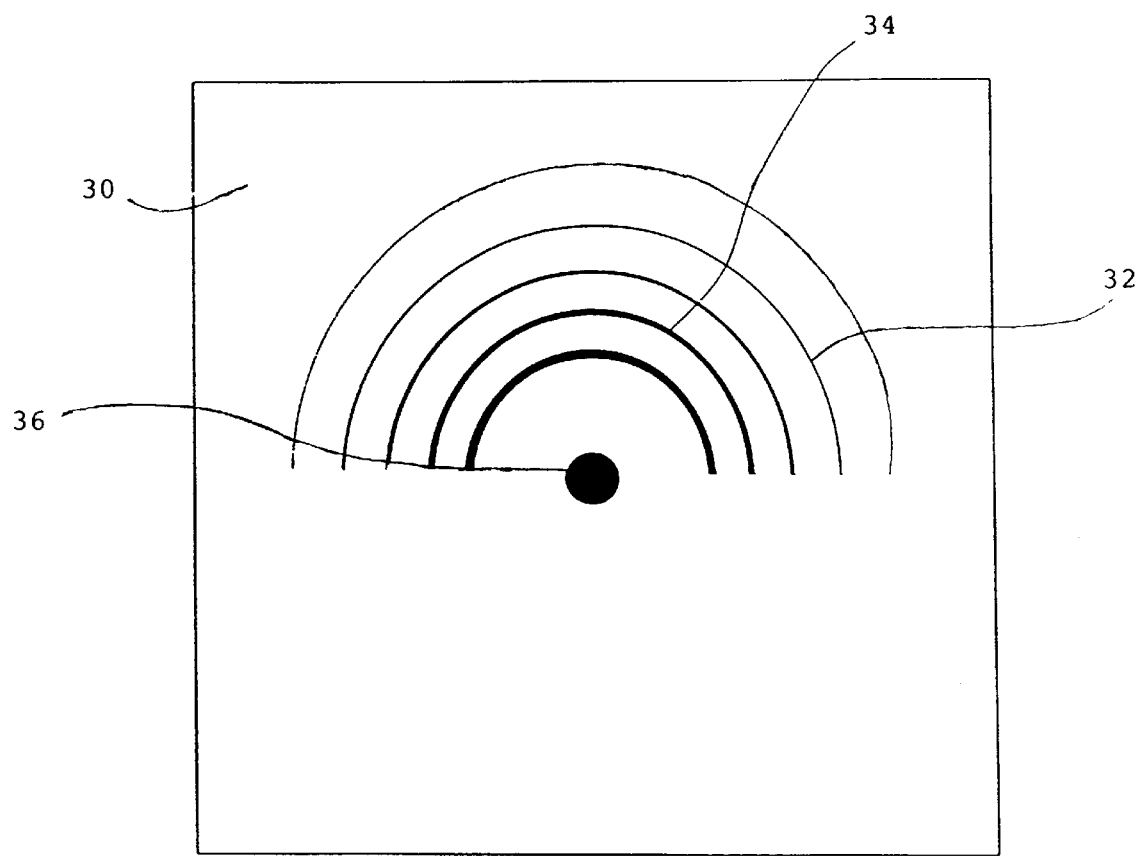
FIG. 2 depicts the Receiving Plate of the Laser Receiver.

As illustrated in FIG. 2, a laser particle sizer system is used to determine the atomization for a given spray. Preferably a system using the Fraunhofer diffraction technique, such as the Malvern Particle Sizer System manufactured by Malvern Instruments of Southborough, Mass., is used to determine the atomization. Other methods may also be used in determining atomization such as a Phase Doppler Particle Analyzer (PDPA). PDPA systems are not preferred, since the systems are larger, bulkier and much more complicated to operate and set-up than the Fraunhofer diffraction system. Also, the cost of a PDPA system greatly exceeds that of the Fraunhofer system.

Referring to FIG. 2, the preferred Fraunhofer diffraction system includes a receiver 40 having a receiving plate 30 with a series of light energy sensitive diodes 32, 34 including a single center diode 36. When a droplet enters the laser path 48 (as depicted in FIG. 1), a portion of the laser 48 light energy is diffracted. Smaller droplets diffract the light energy at large angles and, therefore, the receiving plate 30 receives the diffracted light energy at the outer diodes 32. Larger droplets diffract the light energy at smaller angles and, therefore, the diodes 34 closer to the center diode receive the diffracted light energy. The laser diode 32, 34, 36 response signals are then sent to the computer 44 (as depicted in FIG. 1). The computer 44 collects the response signal data, converts the data into droplet size information and computes the mean droplet size, droplet size range, droplet size distribution and preferably Sauter Mean Diameter (SMD).

The Sauter Mean Diameter $D_{32}$ can be obtained by combining the volume mean diameter $D_{30}$ and the surface mean diameter $D_{20}$ such that $D_{32}=D_{30}^3/D_{20}^2$. The Sauter Mean Diameter is defined as the diameter of a drop having the same volume/surface ratio as the entire spray. The Sauter equation provides a convenient and fairly accurate representation of the atomized spray. Although the Sauter Mean Diameter equation has been described as the preferred method of characterizing the atomized spray, other equations or representations may also be used to describe the spray.

The method of optimization is comprised of the following steps. First, atomization 26 is measured at various gas pressures while maintaining a constant liquid flow rate. A graphical representation of the relationship between atomization 26 and gas pressure can be produced. Next, transfer efficiencies should be experimentally determined using the standards of the American Society of Testing and Materials (ASTM), and preferably the standard issued under the fixed designation D 5327, *Standard Practice for Evaluating and Comparing Transfer Efficiency Under General Laboratory Conditions*. The transfer efficiencies are determined at various gas pressures while maintaining a constant liquid flow rate.

Figure 3:
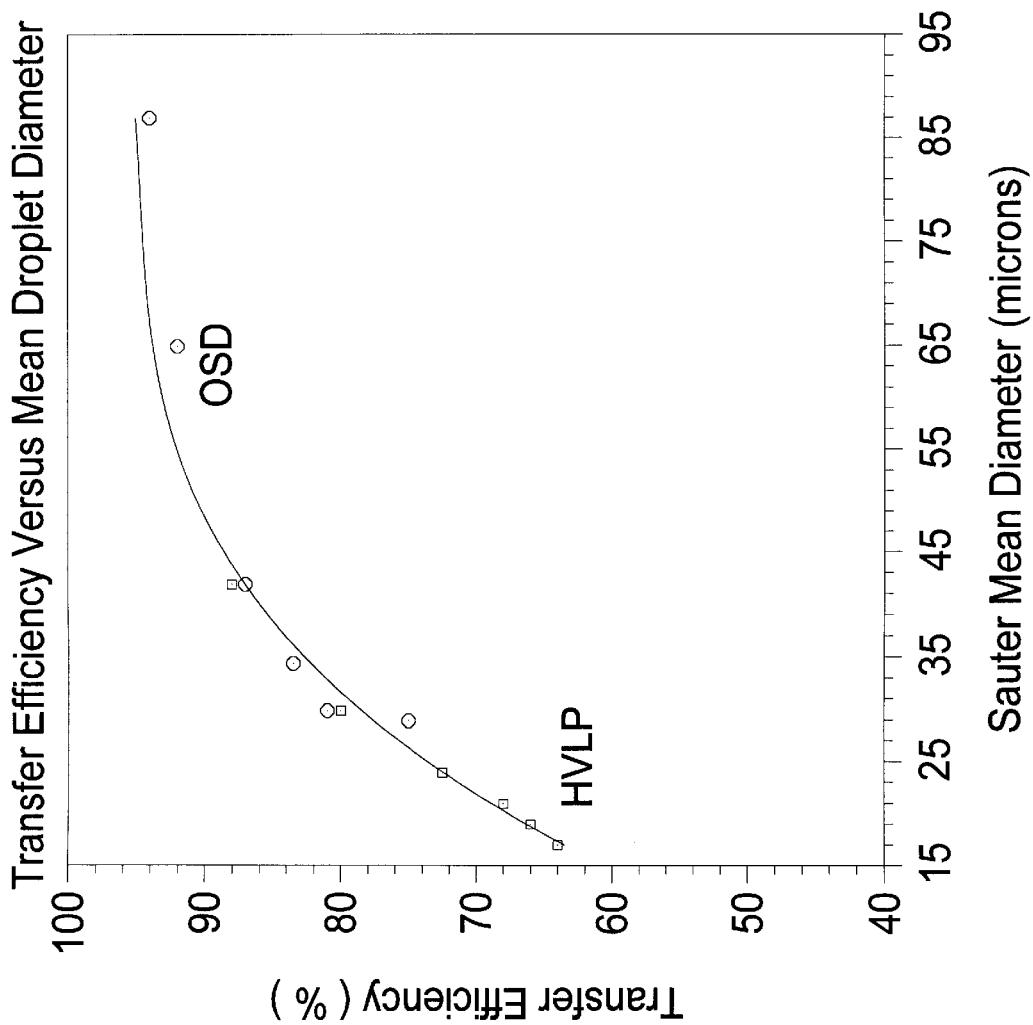
FIG. 3 is a graph depicting the cross correlated transfer efficiency and atomization data for the HVLP and CAS systems.

The relationship between transfer efficiency and gas pressure can also be graphically represented and used as a reference. In general, for any given atomization there is a corresponding transfer efficiency, and this relationship is independent of the spray system or spray gun configuration, as illustrated in FIG. 3. The FIG. 3 graph illustrates a curve whose coordinates are expressed as a cross correlation between transfer efficiency and atomization 26 utilizing gas pressure as a reference, so that a gas pressure X corresponds to a transfer efficiency Y and an atomization Z. While two different spray systems were used, the experimental results for both systems follow the same curve. Therefore, once a graph is completed for a range of transfer efficiencies and corresponding atomizations there is no longer a need to experimentally measure the transfer efficiency for the tested liquid coating or compounds having very similar characteristics.

In an alternative embodiment of the present invention a graph of the cross correlated data is first compiled using experimental data gathered for a tested liquid. Once the data is graphed and correlated the transfer efficiencies and their corresponding atomizations become apparent for the tested liquid. The optimized atomization is then determined as the atomization that corresponds to the desired transfer efficiency. Once the optimized atomization is chosen, the atomization of the CAS system is monitored and measured at various pressures until the optimized atomization is achieved. Once the optimization atomization is achieved the corresponding air pressure reading and flow rate are recorded. Knowing the optimized air pressure and flow rate, the CAS air pressure and flow rate can then be set to the optimized readings to produce the optimized spray.

What is claimed is:

1. A method for optimizing a CAS spray device comprising the following steps:
   (a) regulating and measuring a pressurized air being supplied to the CAS spray device;
   (b) regulating and measuring a liquid flow rate being supplied to the CAS spray device;
   (c) measuring an atomization of sprays produced by the CAS spray device at various air pressures and liquid flow rates;
   (d) experimentally measuring a transfer efficiency of atomized sprays having desirable spray characteristics at various air pressures;
   (e) cross correlating the atomization and the transfer efficiency using air pressure as a reference;
   (f) selecting a desired transfer efficiency;
   (g) determining an optimized atomization corresponding to the desired transfer efficiency using the cross-correlated data; and
   (h) adjusting the CAS spray device apparatus to achieve the optimized atomization.

2. The method for optimizing the spray device as recited in claim 1, wherein the step of measuring the transfer efficiency of atomized sprays includes determining the percent of a coating gained on a workpiece relative to the weight of a coating sprayed.

3. The method for optimizing the spray device as recited in claim 1, wherein the step of adjusting the CAS spray device includes:
   (a) measuring the atomization of sprays produced by the CAS spray device at various air pressures and liquid flow rates;
   (b) recording the air pressure and the liquid flow rate for a spray having the optimized atomization; and
   (c) regulating the air pressure and liquid flow rate to produce a spray having the optimized atomization.

4. The method for optimizing the spray device as recited in claim 1, wherein the step of measuring the atomization includes passing a laser beam perpendicular to and through the path of an atomized spray and producing a response signal by determining the diffraction of the laser beam as it passes through droplets within the atomized spray.

5. The method for optimizing the spray device as recited in claim 4, wherein the step of measuring the atomization includes converting the response signal into droplet size data and determining a mean droplet size, a droplet size range, a droplet size distribution, and a Sauter Mean Diameter from the droplet size data.

6. The method for optimizing the spray device as recited in claim 1, wherein the step of measuring the atomization is quantified as a Sauter Mean Diameter.

7. The method for optimizing the spray device as recited in claim 1, wherein the step of regulating and measuring the pressurized air supplied to the spray device includes:
   (a) supplying the pressurized air;
   (b) regulating the supplied pressurized air;
   (c) controlling a gas mass flow rate and the air pressure of the regulated supplied pressurized air to produce an actuated pressurized air; and
   (d) measuring the pressure of the actuated pressurized air and delivering a measured actuated pressurized air to a spray applicator.

8. The method for optimizing the spray device as recited in claim 1, wherein the step of measuring the liquid flow rate includes:
   (a) supplying a volume of liquid;
   (b) delivering and controlling the volume of liquid to a spray applicator;
   (c) measuring the liquid flow rate as the liquid being delivered to the spray applicator; and
   (d) producing and applying a liquid spray to a workpiece.

9. The method for optimizing the spray device as recited in claim 1, wherein the step of measuring the atomization of the sprays includes measuring the atomization at various air pressures for a selected liquid flow rate.

10. The method for optimizing the spray device as recited in claim 1, further including:
    (a) determining the pressure of a liquid being delivered to a spray applicator;
    (b) diverting the liquid from the spray applicator once the determined pressure is elevated to a preset level; and
    (c) delivering the diverted liquid to a metering pump.

11. An apparatus for optimizing a CAS spray device comprising:
    (a) means for regulating and measuring a pressurized air being supplied to the CAS spray device;
    (b) means for regulating and measuring a liquid flow rate being supplied to the CAS spray device;
    (c) means for measuring an atomization of sprays produced by the CAS spray device at various air pressures and liquid flow rates;
    (d) means for experimentally measuring a transfer efficiency of atomized sprays having desirable spray characteristics at various air pressures;
    (e) means for cross correlating the atomization and the transfer efficiency using air pressure as a reference;
    (f) means for selecting a desired transfer efficiency;
    (g) means for determining an optimized atomization corresponding to the desired transfer efficiency using the cross-correlated data; and
    (h) means for adjusting the CAS spray device apparatus to achieve the optimized atomization.

12. The apparatus for optimizing the spray device as recited in claim 11, wherein the means for measuring the transfer efficiency of atomized sprays includes means for determining the percent of a coating gained on a workpiece relative to the weight of a coating sprayed.

13. The apparatus for optimizing the spray device as recited in claim 11, wherein the means for adjusting the CAS spray device includes:
    (a) means for measuring the atomization of sprays produced by the CAS spray device at various air pressures and liquid flow rates;
    (b) means for recording the air pressure and the liquid flow rate for a spray having the optimized atomization; and
    (c) means for regulating the air pressure and liquid flow rate to produce a spray having the optimized atomization.

14. The apparatus for optimizing the spray device as recited in claim 11, wherein the means for measuring the atomization includes a transmitter housing a laser, the laser passing a laser beam perpendicular to and through the path of the spray and producing a diffracted laser light, a receiver receiving the diffracted laser light and producing a response signal.

15. The apparatus for optimizing the spray device as recited in claim 14, wherein the means for measuring the atomization includes a computer receiving the response signal, the computer converting the response signal into droplet size data and determining a mean droplet size, a droplet size range, a droplet size distribution, and a Sauter Mean Diameter from the droplet size data.

16. The apparatus for optimizing the spray device as recited in claim 11, wherein the means for measuring the atomization includes means for quantifying the atomization as a Sauter Mean Diameter.

17. The apparatus for optimizing the spray device as recited in claim 11, wherein the means for regulating the pressurized air supplied to the spray device includes:
   (a) a pressure regulator means for controlling an air pressure, the pressure regulator means being fluidly connected to an air supply source;
   (b) an actuated control valve means for controlling a gas mass flow rate and gas pressure, the actuated control valve means being fluidly connected to the pressure regulator means;
   (c) a pressure measuring means for measuring a pressure, the pressure measuring means being fluidly connected to the actuated control valve means; and
   (d) a spray application means for applying a spray, the spray application means being fluidly connected to the pressure measuring means.

18. The apparatus for optimizing the spray device as recited in claim 11, wherein the means for measuring the liquid flow rate includes:
   (a) a fluid pot means for holding a volume of liquid;
   (b) a metering pump means for delivering and controlling the volume of liquid, the metering pump means being fluidly connected to the fluid pot means;
   (c) a mass flow meter means for measuring the liquid, the mass flow meter being fluidly connected to the metering pump means; and
   (d) a spray application means for applying a spray, the spray application means being fluidly connected to the mass flow meter means.

19. The apparatus for optimizing the spray device as recited in claim 11, wherein the means for measuring the atomization of the CAS atomized spray includes means for measuring the atomization at various air pressures for a selected liquid flow rate.

20. The apparatus for optimizing the spray device as recited in claim 11, further including:
   (a) a pressure relief valve for diverting a liquid;
   (b) a spray applicator fluidly connected to the pressure relief valve;
   (c) a metering pump having an inlet and an outlet, the inlet fluidly connected to the relief valve and the outlet fluidly connected to the relief valve and the outlet also being fluidly connected to the spray applicator; and
   (d) the relief valve opening upon determining a preset pressure increase whereby liquid is diverted from the spray applicator and into the inlet of the metering pump.

21. An apparatus for optimizing a CAS spray device comprising:
   (a) a laser particle sizing apparatus for determining and analyzing an atomization of sprays at various air pressures;
   (b) means for measuring a transfer efficiency of atomized sprays at various air pressures;
   (c) a liquid system side including:
      (i) a liquid supply source,
      (ii) a metering pump fluidly connected to the liquid supply source,
      (iii) a mass flow meter fluidly connected to the metering pump, and
      (iv) a spray applicator fluidly connected to the mass flow meter, the spray applicator producing the spray; and
   (d) a gas system side including:
      (i) an air supply source,
      (ii) an actuated pressure regulator fluidly connected to the air supply source,
      (iii) a flow rate control and measurement instrument fluidly connected to the actuated pressure regulator,
      (iv) an actuated control valve fluidly connected to the flow rate control and measurement instrument, and
      (v) an outgoing pressure measurement instrument fluidly connected to the actuated control valve and also fluidly connected to the spray applicator;
   (e) the liquid system side and the gas system side having fluid flow parameters selected and controlled so that, when the atomization and the transfer efficiency are cross correlated using air pressure as a reference and an optimized atomization is determined from the cross-correlated data corresponding to a desired transfer efficiency, the CAS spray device achieves and maintains the optimized atomization.

22. The apparatus for optimizing the spray device as recited in claim 21, wherein the laser particle sizing apparatus includes a transmitter housing a laser, the laser passing a laser beam perpendicular to and through the path of the spray and producing a diffracted laser light, and a receiver for receiving the diffracted laser light and producing a response signal.

23. The apparatus for optimizing the spray device as recited in claim 22, wherein the laser particle sizing apparatus further includes a computer receiving the response signal from the receiver, the computer converting the response signal into a droplet size data and determining a mean droplet size, a droplet size range, a droplet size distribution, and a Sauter Mean Diameter from the droplet size data.

24. The apparatus for optimizing the spray device as recited in claim 21, further including:
   (a) a pressure relief valve for diverting a liquid;
   (b) the spray applicator fluidly connected to the pressure relief valve;
   (c) the metering pump having an inlet and an outlet, the inlet fluidly connected to the relief valve and the outlet fluidly connected to the relief valve and the outlet also being fluidly connected to the spray applicator; and
   (d) the relief valve opening upon determining a certain increased pressure whereby the liquid is diverted from the spray applicator and into the inlet of the metering pump.

25. A method for optimizing a CAS spray device comprising the following steps:
   (a) measuring an atomization for a range of known air pressures at a constant liquid flow rate to produce a determined atomization;
   (b) determining a transfer efficiency for the range of known air pressures at the constant liquid flow rate to produce a determined transfer efficiency;
   (c) cross correlating the determined atomization and the determined transfer efficiency using the known air pressures as a reference to produce a cross correlated atomization and transfer efficiency;

(d) optimizing the cross-correlated atomization and transfer efficiency to determine an optimized transfer efficiency by determining a corresponding atomization at which a desired transfer efficiency occurs on the cross correlation.

(e) determining the known gas pressure at which the desired transfer efficiency occurs to produce an optimized air pressure; and (f) regulating a pressurized air supply to deliver air at the optimized air pressure to the spray device.

26. The method for optimizing the spray device as recited in claim 25, wherein the step of measuring the atomization includes the following steps:

(a) passing a laser beam perpendicular to and through the path of an atomized spray; and (b) producing a response signal by determining the diffraction of the laser beam as the beam passes through droplets within the atomized spray.

27. The method for optimizing the spray device as recited in claim 26, wherein the step of measuring the atomization includes:

(a) delivering the response signal to a computer for processing;

(b) converting the response signal into droplet size data; and (c) determining a mean droplet size, a droplet size range, a droplet size distribution, and a Sauter Mean Diameter from the droplet size data.

28. The method for optimizing the spray device as recited in claim 25, wherein the step of determining the transfer efficiency includes determining the percent of a coating gained on a sprayed part relative to the weight of a coating sprayed.

29. The method for optimizing the spray device as recited in claim 25, wherein the step of determining the known gas pressure includes determining the known gas pressure for a corresponding atomization at which a desired transfer efficiency occurs.

* * * * *